United States Patent
Nierle et al.

(10) Patent No.: US 7,256,234 B2
(45) Date of Patent: Aug. 14, 2007

(54) HYBRID SYSTEM FOR SOLUBILIZING PHARMACEUTICALLY ACTIVE SUBSTANCES IN POLYMER MATRICES

(75) Inventors: Jens Nierle, Hamburg (DE); Christian Gäde, Neu Wulmstorf (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 10/948,763

(22) Filed: Sep. 22, 2004

(65) Prior Publication Data

US 2005/0124743 A1  Jun. 9, 2005

Related U.S. Application Data

(63) Continuation of application No. PCT/EP03/02953, filed on Mar. 21, 2003.

(30) Foreign Application Priority Data

Mar. 22, 2002 (DE) .................. 102 12 864

(51) Int. Cl.
- A61F 13/00 (2006.01)
- A61F 13/02 (2006.01)
- A61L 15/15 (2006.01)
- A61L 15/03 (2006.01)
- A61K 9/00 (2006.01)
- A61K 9/70 (2006.01)

(52) U.S. Cl. .......... 524/502; 524/502; 424/448; 424/449; 424/405; 514/58; 514/944; 514/946; 604/897; 604/896; 604/892; 604/890

(58) Field of Classification Search .......... 524/502; 514/58; 424/448, 449
See application file for complete search history.

(56) References Cited

U.S. PATENT DOCUMENTS

| | | | |
|---|---|---|---|
| 5,120,546 A * | 6/1992 | Hansen et al. ............ 424/449 |
| 5,126,144 A | 6/1992 | Jaeger et al. | |
| 5,246,582 A | 9/1993 | Sluma et al. | |
| 5,273,757 A | 12/1993 | Jaeger et al. | |
| 5,306,502 A | 4/1994 | Jaeger et al. | |
| 5,411,739 A * | 5/1995 | Jaeger et al. ............. 424/448 |
| 5,702,720 A * | 12/1997 | Effing et al. ............. 424/448 |
| 5,906,830 A | 5/1999 | Farinas et al. | |
| 6,024,975 A * | 2/2000 | D'Angelo et al. .......... 424/449 |
| 6,221,383 B1 | 4/2001 | Miranda et al. | |
| 6,703,043 B1 * | 3/2004 | Himmelsbach et al. ..... 424/449 |
| 2003/0099695 A1 | 5/2003 | Mueller | |

FOREIGN PATENT DOCUMENTS

| | | |
|---|---|---|
| DE | 199 08 787 A1 | 9/2000 |
| JP | 63-097202 | 4/1988 |
| JP | 63097272 A | 4/1994 |
| WO | 89/01789 | 3/1989 |
| WO | 94/23713 A1 | 10/1994 |
| WO | WO94/23713 A1 | 10/1994 |
| WO | 97/10812 | 3/1997 |

OTHER PUBLICATIONS

International Search report dated Jul. 30, 2003, from corresponding International Application No. PCT/EP03/02953.
English Language Abstract of JP 63-097202, Apr. 27, 1988.
Kleben & Dichten, No. 42, 1998, pp. 26-30, no date.

* cited by examiner

*Primary Examiner*—Duane Smith
*Assistant Examiner*—Ives Wu
(74) *Attorney, Agent, or Firm*—Greenblum & Bernstein, P.L.C.

(57) ABSTRACT

The present invention is directed to a hybridized polymer matrix, a method of making such, and products incorporating such a matrix. The hybridized polymer matrix comprises a solvent-free polymer matrix base, a hybridized matrix comprising one or more poly(1-vinyl-2-pyrrolidones) and dimethyl sulfoxide, and at least one active substance. The hybridized polymer matrix is useful in the preparation of transdermal therapeutic systems, particularly making possible the introduction of pharmaceutically active substances which are otherwise difficult to dissolve, such as ibuprofen, into a non-polar matrix.

22 Claims, No Drawings

HYBRID SYSTEM FOR SOLUBILIZING PHARMACEUTICALLY ACTIVE SUBSTANCES IN POLYMER MATRICES

CROSS-REFERENCE TO RELATED APPLICATIONS

This application is a continuation of PCT/EP03/02953, filed Mar. 21, 2003, which is incorporated herein by reference in its entirety, and also claims the benefit of German Priority Application No. 102 12 864.2, filed Mar. 22, 2002.

FIELD OF THE INVENTION

The present invention relates to hybrid systems comprising as their components polyvinylpyrrolidone and/or copolymers thereof and dimethyl sulfoxide. Additionally the invention embraces polymer matrices comprising these hybrid systems, transdermal therapeutic systems based on the polymer matrices, and production thereof. The hybrid system makes it possible to introduce pharmaceutically active substances which are otherwise difficult to dissolve, ibuprofen being one example, into a non-polar matrix. The advantage of the system is that it allows polar active substances to be dissolved to beyond the saturation point in a non-polar matrix such as, for example, polyisobutylene. In addition the hybrid system prevents the active substance crystallizing, thereby ensuring constant release of the active substance throughout the pre-expiry life of a transdermal system, such as patches, for example.

BACKGROUND OF THE INVENTION

In the formulation of medicinal products for the topical application of active substances the choice of excipients is of critical importance. It is known, for instance, that there is a correlation between the solubility of an active substance in a vehicle and its release from that vehicle. When a vehicle containing active substance is applied to the skin, an equilibrium is established in the partition of the active substance between vehicle and skin. The position of this equilibrium is determined by the solubility in both phases.

Transdermal therapeutic systems (TTS) for delivering active substances through the skin have been known for a long time. The topical application of drugs by way of active substance patch systems offers two main advantages: firstly this form of administration produces first-order release kinetics of the active substance, thereby enabling a constant level of active substance to be maintained in the body over a very long period. Secondly the path of uptake through the skin avoids the gastrointestinal tract and also the first liver passage. As a result, selected drugs can be administered effectively in a low dose. This is particularly advantageous when the drug is desired to act locally, with avoidance of a systemic effect. This is the case, for example, with the treatment of rheumatic joint complaints or muscular inflammation.

One embodiment of such transdermal systems which has been well described in the technical literature is that of matrix systems or monolithic systems in which the drug is incorporated directly into the pressure-sensitive adhesive. In the ready-to-apply product a pressure-sensitive adhesive matrix of this kind, comprising active substance, is equipped on one side with a backing, which is impermeable to the active substance, while on the opposite side there is a backing film equipped with a release layer, which is removed prior to application to the skin (Kleben & Dichten, No. 42, 1998, pp. 26 to 30). Thus mention is made principally of the use of polyacrylates and/or polyurethanes as a basis for the pressure-sensitively adhesive polymer matrix (Lambda, Woodhouse, & Cooper, "Polyurethanes in Biomedical Applications", CRC Press, 1998, p. 240) and WO 01/68060.

A problem associated with the production of transdermal therapeutic systems is the introduction of polar active substances into the generally non-polar polymer matrices. As a result it is possible for preferred active substances to be incorporated sometimes only with difficulty or only in a limited concentration into the polymer matrix. The risk exists, moreover, that because of the difference in polarity and insolubility of the active substances in the polymer matrix, the active substances will, over time, crystallize out of the polymer system. Long-term stability is therefore not ensured.

One proposal for solving these problems is provided by the addition of solvent. The incorporation of solvent into a polymer matrix, however, has a variety of drawbacks. These include the harmful nature of the generally organic solvents, high levels of technical effort involved in suction extraction and recovery, high costs for the high-purity solvents that are necessary, and, in particular, a very high level of effort required for removing solvent residues from the matrix.

These solvents are likewise absorbed through the skin, thereby lowering the solvent content of the TTS matrix. Additionally it has been found that water given off by the skin accumulates in the solvent, since it cannot be readily bound by the hydrophobic polymer matrix. Both mechanisms result in an adverse effect on the release of active substance.

WO 01/68060 A2 describes a transdermal therapeutic system of the matrix type, where polyacrylate polymers are mixed in the with the hydrophobic base polymers of the active substance-containing polymer matrix. The hydrophobic base polymers may be selected from the group consisting of polysiloxanes, polyisobutylene, polyisoprene, styrene-diene-styrene block copolymer or mixtures thereof. The polyacrylate polymers are said to avoid the drawback of the supersaturation of the active substance in the TTS as a result of the addition of solvent, and to prevent recrystallization prior to absorption through the skin.

WO 94/23713 describes anti-inflammatory drugs based on phenylpropionic acid and phenylacetic acid for topical application, comprising combinations of lipophilic and hydrophilic excipients. No details are given of the mode of action or function of said excipients.

SUMMARY OF THE INVENTION

It is an object of the present invention to develop a system which allows polar active substances to be taken up in non-polar polymer matrices and prevents the crystallization of the active substances in the non-polar polymer matrices, without the use of additional solvents.

Patch systems containing active substance are subject not only to the requirement of controlled release of active substance but also to certain requirements relating to the adhesive matrix, such as its skin-friendly nature, effective adhesion over a long period of application, and painless removability, for example. A frequently observed side-effect, however, particularly in the case of polyacrylate adhesive matrices, is the appearance of skin irritations, which occur in particular when an active substance patch is applied for a relatively long period, or repeatedly, to the same region of the body. The principal cause of these irritations are the ingredients of the pressure-sensitively adhesive matrix. Painful detachment of the active substance patch following a prolonged period of wear is also frequently observed. The addition of further adhesives, which under certain circumstances give rise to side-effects such as maceration, allergies, etc., should therefore not be practiced.

Active substance patches are generally applied to healthy, intact skin. Here in particular it is especially important that the intact skin is not irritated, let alone damaged, by a drug. Furthermore, sufficient cohesiveness is necessary, in order to be able to remove the active substance patch without residue and also in particular without pain after the period of wear is at an end.

It is therefore an object of the present invention to provide a transdermal therapeutic system which allows the user the maximum possible comfort, i.e., long period of wear, skin-gentle application and painless detachment.

The specified objects are achieved by means of a hybrid system composed of polyvinylpyrrolidone (PVP) and/or copolymers thereof and dimethyl sulfoxide (DMSO), polymer matrices comprising this hybrid system, and the TTS constructed therewith, in accordance with the main claims. Further claims provide advantageous embodiments of the inventive systems and matrices. The invention further embraces the process for producing such hybrid systems, matrices and transdermal therapeutic systems.

DETAILED DESCRIPTION OF THE PREFERRED EMBODIMENTS

It was surprising and could not have been foreseen by the skilled worker—and therein lies the solution of said objects—that a hybrid system composed of the combination of polyvinylpyrrolidone (PVP) and/or copolymers thereof and dimethyl sulfoxide (DMSO) would allow polar active substances to be taken up into non-polar polymer matrices and would prevent the crystallization of the active substances in the non-polar polymer matrices, without the use of additional solvents.

The hybrid system of the invention comprises poly(1-vinyl-2-pyrrolidones) of the general formula

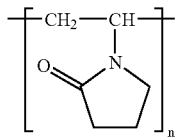

with n=350 to 13,500, and/or copolymers thereof, and dimethyl sulfoxide.

The weight ratio of poly(1-vinyl-2-pyrrolidones) and/or copolymers thereof and dimethyl sulfoxide is preferably in the range from 1:99 to 99:1, in particular from 20:80 to 80:20, especially 50:50.

It is to be regarded as even more advantageous if poly(1-vinyl-2-pyrrolidones) and/or copolymers thereof have an average molecular weight of from 2000 to 1,500,000 g/mol, in particular from 44,000 to 54,000 g/mol.

The combination of the two compounds to form a hybrid system proves to be extremely advantageous for a wide variety of fields of use, such as, among other things, as solubilizers of polar active substances in non-polar polymer matrices.

Preferred polymer matrices are compositions which include no solvent at all. Particular preference is given to what are called hot melt compositions. Hot melt adhesives allow disadvantages associated with the necessary use of solvents in the case of conventional adhesives containing active substance to be avoided. The use of hot melt adhesives advantageously allows the use of thermoplastic hot melt self-adhesive compositions based on natural and synthetic rubbers and on other synthetic polymers such as acrylates, methacrylates, polyurethanes, polyolefins, polyvinyl derivatives, polyisobutylenes, polyesters or silicones. Additives such as tackifier resins, plasticizers, stabilizers and other auxiliaries may be added as far as is necessary.

The advantages of the hot melt adhesives in the context of the preparation of adhesives comprising active substance have been described in the patent literature for a number of years already (see for example EP 0 305 757 A1).

In order to ensure functionally appropriate use, the hot melt adhesives may be foamed, and are preferably foamed with inert gases such as nitrogen, carbon dioxide, noble gases, hydrocarbons or air, or mixtures of these. In some cases, foaming additionally by thermal decomposition of gas-evolving substances, such as azo, carbonate, and hydrazide compounds, has proven appropriate.

The degree of foaming, i.e., the gas content, should be at least about 5% by volume and can range up to about 50% by volume. In practice, levels of from 10% to 35%, preferably 15%, by volume have been found appropriate. Operating at relatively high temperatures of approximately 100° C. and with a comparatively high internal pressure produces very open-pored adhesive foam layers which are particularly permeable to air and water vapor. A degree of foaming of more than 50% by volume is regarded as being technically impracticable, since it reduces the cohesion of the composition.

From the multiplicity of known polymer matrices, polyisobutylenes are particularly preferred. Polyisobutylenes as the matrix base fulfill the requirements of a self-adhesive, skin-gentle and painlessly detachable polymer matrix with particular effectiveness, and so it is logical to select the polyisobutylenes with preference as a matrix base.

As the polyvinylpyrrolidone (PVP) component, it is possible, for example, to use Luviskol and Kollidon from BASF, preferably in an amount of 0.25%–60% by weight, more preferably between 1% and 30% by weight. To the same extent it is also possible to use PVP copolymers such as, for example, vinylpyrrolidone-vinyl acetate (povidone acetate; Kollidon VA 64, terpolymers based on vinylpyrrolidone and acrylic acid or methacrylic acid and/or esters thereof (Luviflex VBM 35), copolymers of vinylpyrrolidone and vinylimidazolium methochloride (Luviquat brands) as the so-called PVP agent.

The system is particularly functional in gel form. It can also be employed in another form, such as that of an emulsion, or both components are incorporated individually, in succession, into the system. It is important for the stability of the composition that both components are present in the system.

It is in the combination of the two compounds, PVP and/or copolymers thereof and DMSO, that there lies the unforeseeable, advantageous step to achieving the stated objects. Only both compounds provide, synergistically, the desired effect of the integration of polar active substances into non-polar polymer matrices. The use of either compound alone is unsuccessful. Dimethyl sulfoxide is too polar and after a short period of storage reemerges from the polymer matrix. This effect would result in a very sharp drop in the bond strength of the matrix, which is undesirable for a long period of residence on the skin. PVP is insoluble in non-polar polymers, especially polyisobutylene, and would be present in the form of spherical inclusions. Only through the preparation of the PVP/DMSO hybrid system, formulated advantageously as a gel, is it possible to integrate the two components completely into the non-polar matrix. Neither emergence of the DMSO from the matrix nor deterioration in the bond strength is found. Furthermore it is possible for the PVP and/or copolymers thereof to form coordination compounds with fillers that are present in the matrix, provided such fillers possess polar groups, such as hydroxyl groups, for example. By way of the N-functionality of the PVP it is possible in this way for active substances and/or fillers to be associated. The association is supported by the effective solution properties of the DMSO. This produces a synergistic effect on the part of the two agents. The associating fillers may include, among others, various types of cellulose. By way of example it is possible to use pulverulent celluloses, such as Elcema P020 from Degussa, and also microcrystalline cellulose. By coordinating the PVP with the cellulose it is possible to make the system significantly harder as compared with the PVP-free systems. This effect leads to a further improvement in the compatibility of the PVP/DMSO hybrid system with the polymer matrix.

A further substantial advantage of the hybrid system of the invention and its use in polymer matrices is its control of various physical properties of the matrix by way of the amount of the PVP/DMSO system employed, such as, for example, the hardness or flexibility of the composition. The hardness of the system can additionally be controlled by way of the degree of polymerization of the PVP, with too high a degree of polymerization of the PVP resulting in harder compositions. Consequently the degree of polymerization is subject to certain restrictions. Likewise it is possible to vary the adhesion in conjunction with a relatively high skin moisture content. The patch is occlusive. PVP as film former takes up water, so that the compositions are able to attach to the skin very effectively and adhere strongly. The preferred amount of the hybrid system of the invention in polymer matrices is between 2% and 9% by weight, based on the total mass of the matrix, including active substance.

PVP is regarded as very substantially inert, so that there is no likelihood of chemical reactions with the pharmaceutically active substances in the polymer matrix. In contrast to the solvent-based system described in WO 01/68060, and polyacrylates, PVP cannot be employed in pure form in a hot melt operation if using non-polar polymers as the matrix. In that case, as described above, the dissolution of the PVP in the matrix is poor. In the solvent-based operation, in contrast, alcohols are used as solvents. These solvents lead to swelling of the PVP. Although as a result the base material develops its film-forming properties and can be incorporated homogeneously into the composition, and although this homogeneous state is retained even after the necessary removal of the solvent, the drawbacks of solvent-borne systems are known. The system of the invention manages without additional solvent, since a film or gel is developed by way of the DMSO, and, promoted by the DMSO, the PVP is present as a "film" in the matrix.

The PVP film as such is very advantageous in the context of the solubility of the active substance.

The hybrid system of the invention comprising PVP and/or copolymers thereof and DMSO has very good dissolution properties for polar active substances such as ibuprofen for example. The effective solubilization of the hybrid system of the invention for active substances in non-polar matrices derives on the one hand from the fact that acidic active substances are able to coordinate with the nitrogen functions of the PVP and on the other hand from the fact that dimethyl sulfoxide in the gel or hybrid system possesses a very high solubility potential. The stabilization of the active substance with respect to crystallization from the matrix is synergistically reinforced as a result of both properties.

Ibuprofen is (±)-2-(4-isobutylphenyl)propionic acid ($C_{13}H_{18}O_2$; $M_R$ 206.28; melting point 75 to 77° C.) with the general formula

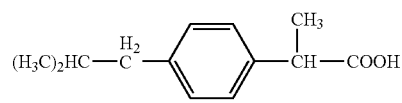

(according to Römpp Lexikon Chemie, Version 1.3, Stuttgart, New York: Georg Thieme Verlag 1997). Ibuprofen is a known active substance having analgesic and anti-inflammatory properties and is therefore employed for soft-tissue rheumatism and inflammatory joint disorders. The active substance is mostly used in the form of tablets or suppositories. Oral administration may, however, lead to side effects such as nausea, vomiting, dizziness and headaches. For that reason ibuprofen must not be taken by patients having gastric ulcers.

Following topical application the active substance reaches the target without being metabolized by the liver beforehand. This makes it possible to avoid disadvantages such as the first-pass effect and side effects associated with the oral or rectal administration of ibuprofen. Release of the active substance from an adhesive matrix has further advantages as compared with conventional topical administration forms such as creams or ointments. The active substance is released continuously from the matrix and is not administered in single doses. If unwanted side effects occur the active substance patch can simply be removed and thus the delivery of ibuprofen stopped.

The inventive concept therefore also embraces active substance patches comprising a backing material and inventive hot melt adhesive applied at least partially thereon, characterized in that the hot melt adhesive comprises ibuprofen.

The quantitative concentrations of the ibuprofen in the hot melt adhesive are preferably between 0.01% to 50% by weight, preferentially from 0.1% to 20% by weight.

Besides the ibuprofen referred to above it is also possible to incorporate further active substances into the composition by means of the system recited above. Typical active substances in the polymeric adhesive are—without making any claim to completeness in the context of the present invention:

| Indication: | Active substance |
|---|---|
| Antimycotics | Nafitine |
| | Amorrolfine |
| | Tolnaftate |
| | Ciclopirox |

-continued

| Indication: | Active substance |
|---|---|
| Antiseptics | Thymol |
| | Eugenol |
| | Triclosan |
| | Hexachlorophene |
| | Benzalkonium chloride |
| | Clioquinol |
| | Quinolinol |
| | Undecenoic acid |
| | Ethacridine |
| | Chlorhexidine |
| | Hexetidine |
| | Dodicine |
| | Iodine |
| Nonsteroidal antirheumatics | Glycol salicylate |
| | Flufenamic acid |
| | Ibuprofen |
| | Etofenamate |
| | Ketoprofen |
| | Piroxicam |
| | Indomethacin |
| Antipruritics | Polidocanol |
| | Isoprenaline |
| | Crotamiton |
| Local anesthetics | Benzocaine |
| Antipsoriatics | Ammonium bitumasulfonate |
| Keratolytics | Urea |
| | Salicylic acid |

Besides these it is also possible to mention hyperemic substances such as natural active substances of cayenne pepper or synthetic active substances such as nonivamide, nicotinic acid derivatives, preferably benzyl nicotinate or propyl nicotinate. The use of various essential oils is a further possibility.

A transdermal therapeutic system (TTS), generally in the form of a patch, comprises an inventive self-adhesive polymer matrix comprising active substance, a backing layer impermeable to active substance, and a detachable protective layer, which is removed before the system is applied to the skin. Further ingredients, such as fillers, stabilizers, enhancers and/or cosmetic additions, may be incorporated in the polymer matrix in order to adapt the TTS to the different fields of application and to provide an application-friendly TTS. The polymer matrix of the invention may be made self-adhesive or non-adhesive. In the latter case, that of an island dressing, for example, there ought, however, to be auxiliary means provided for attachment to the skin.

With particular advantage the polymer matrix of the invention is applied to a flexible outer layer, particularly in the context of its use as a self-adhesive patch.

Transdermal therapeutic systems of this kind acquire a variety of advantages as a result of the polymer matrix of the invention. Thus, for example, very uniform delivery of active substance over a period of up to 24 hours is ensured. The mechanical properties of the patch, including the flexibility and the pressure-sensitive adhesion properties, can to a large extent be influenced by way of the amount of PVP/DMSO gel. The patch absorbs moisture, thereby preventing a film of moisture between adhesive matrix and skin that would constitute an additional barrier to the absorption of the active substance into the skin. As a result of the absorption of liquid, the matrix retains its pressure-sensitive adhesion properties even under increased perspiration. The matrix can additionally be supersaturated with active substance without any crystallization.

A corresponding patch is constructed from a backing such as films, nonwovens, wovens, foams, etc., the adhesive matrix, and liner film, liner paper or release paper for protecting the adhesive matrix prior to service of the patch. In another preferred embodiment of the invention polymer films, nonwovens, wovens and combinations thereof are used as backings. Backing materials available for selection include polymers such as polyethylene, polypropylene and polyurethane or else natural fibers.

In summary it can be stated that all rigid and elastic sheetlike structures of synthetic and natural raw materials are suitable as backing materials. Preference is given to backing materials which can be used in such a way as to realize properties of a functionally compatible dressing. Mention may be made, by way of example, of textiles such as wovens, knits, lays, nonwovens, laminates, nets, films, foams and papers. Additionally these materials may be pretreated and/or aftertreated. Common pretreatments include corona and hydrophobicization; customary aftertreatments are calendaring, heat treatment, lamination, die cutting and wrapping. It is particularly advantageous if the backing material can be sterilized, preferably by means of γ (gamma) radiation.

The stated properties of the adhesive matrix suggest in particular its use for medical products, especially patches, medical fixations, wound coverings, orthopedic or phlebological bandages and dressings.

Finally the polymer matrix can be wrapped with an antiadhesive support material, such as siliconized paper, or provided with a wound contact material or padding. On its self-adhesive composition side, the side which later faces the skin, the patch of the invention is usually lined with an antiadhesive support material over its whole width until the time of service. This support material protects the self-adhesive composition layer of the highly skin-compatible composition of the matrix, which has preferably been applied by a transfer method, and additionally stabilizes the product as a whole. Conventionally the liner can be in one piece or, preferably, of two-part design.

Further embodiments may be such that the TTS has a single-layer or multilayer self-adhesive construction. It is also possible for there to be a second polymer matrix of the invention, possessing higher active-substance solubility, as a reservoir between the reverse face of the matrix and the lining support. On the adhesive side of the matrix there is in part (for example, at the edges) a second matrix of high bond strength for additional fixing, but of inadequate or unnecessary active-substance solubility.

The matrix free of active substance is located between two nonanchoring films and is used for attaching electrodes, etc., or, because of the water absorption capacity, in the case of appropriate geometry, for fixing colostomy/ileostomy bags.

The polymer compositions of the invention are prepared solventlessly. The polymer compositions can be prepared either in a batchwise operation, in a kneading apparatus, or continuously, in an extruder. In the case of preparation in a kneading apparatus the high-polymer material is introduced to start with. The material is prekneaded, for example at 20 rpm and 50.0° C. Subsequently the remaining materials are metered in successively. Between each addition the composition is homogenized for between 15 and 60 minutes, with the liquid components and the active substance being added at the end. After the end of the kneading operation the composition is discharged from the kneading apparatus and can be coated.

Where the composition is extruded, the high-polymer material is first of all metered in via the feed zone and broken down. Then the remaining components are metered in in order, here again the solid components being added first and the liquid components thereafter. The active substance is again metered in as the last component. In contrast to the kneading operation, coating is carried out inline in the case of extrusion.

The examples below illustrate the invention without restricting it. The table below sets out the inventive hybrid systems, polymer matrices and TTS and also their production.

In the examples given, the release of active substance is given from the matrix of the invention on a silicone membrane.

| Gel conc. (%) | Coat weight (g/m$^2$) | Release (μg/cm$^2$) | Release from zero value (%) |
|---|---|---|---|
| Release of Active Substance from Inventive Gel Matrices Onto Silicone Membrane | | | |
| 2 | 335 | 481 | 27.7 |
| Rel. stab. val.: [%] | 2.25 | 1.93 | 2.86 |
| 6 | 342 | 481 | 27.9 |
| Rel. stab. val.: [%] | 0.83 | 2.74 | 3.0 |

EXAMPLE 1

A glass beaker is charged with 20.0 g (50% w/w) of dimethyl sulfoxide, which is heated to 70° C. 20.0 g (50% w/w) of Kollidon 30® are added with stirring. The mixture is stirred at 70° C. for 60 minutes. The finished mixture is in the form of a gel, and is cooled and transferred to a storage vessel.

EXAMPLE 2

A glass beaker is charged with 20.0 g (50% w/w) of dimethyl sulfoxide, which is heated to 70° C. 20.0 g (50% w/w) of Kollidon 90® are added with stirring. The mixture is stirred at 70° C. for 60 minutes. The finished mixture is in the form of a gel, and is cooled and transferred to a storage vessel.

EXAMPLE 3

In an IKA recording extruder 50.35 g (26.5% w/w) of Vistanex LM MH, 22.80 g (12.0% w/w) of Vistanex MM L80 and 21.85 g (11.5% w/w) of Eastoflex PLS E1003D are kneaded at 70° C. for 15 minutes. 60.80 g (32.0% w/w) of pulverulent cellulose are added and the mixture is kneaded for 60 minutes. Thereafter 13.30 g (7.0% w/w) of Cetiol V and 11.40 g (6.0% w/w) of DMSO/PVP mixture are added. The mixture is kneaded for 5 minutes, after which 9.50 g (5.0% w/w) of ibuprofen are added. The resulting mixture is kneaded at 80–100° C. for a further 60 minutes. The finished composition is then pressed out between release paper, using a hydraulic press, and is subsequently laminated to backing and release film.

EXAMPLE 4

In an IKA recording extruder 49.40 g (26.0% w/w) of Vistanex LM MH, 20.90 g (11.0% w/w) of Vistanex MM L80 and 26.60 g (14.0% w/w) of Eastoflex PLS E1003D are kneaded at 70° C. for 15 minutes. 60.80 g (32.0% w/w) of pulverulent cellulose are added and the mixture is kneaded for 60 minutes. Thereafter 19.00 g (10.0% w/w) of Cetiol V and 11.40 g (2.0% w/w) of DMSO/PVP mixture are added. The mixture is kneaded for 5 minutes, after which 9.50 g (5.0% w/w) of ibuprofen are added. The resulting mixture is kneaded at 80–100° C. for a further 60 minutes. The finished composition is then pressed out between release paper, using a hydraulic press, and is subsequently laminated to backing and release film.

EXAMPLE 5

In an IKA recording extruder 41.80 g (22.0% w/w) of Vistanex LM MH, 35.15 g (18.5% w/w) of Vistanex MM L80 and 27.51 g (14.5% w/w) of Eastoflex PLS E1003D are kneaded at 70° C. for 15 minutes. 62.70 g (33.0% w/w) of pulverulent cellulose are added and the mixture is kneaded for 60 minutes. Thereafter 19.00 g (10.0% w/w) of Cetiol V and 11.40 g (2.0% w/w) of DMSO/PVP mixture are added. The mixture is kneaded for 5 minutes, after which 0.095 g (0.05% w/w) of capsaicin are added. The resulting mixture is kneaded at 80–100° C. for a further 60 minutes. The finished composition is then pressed out between release paper, using a hydraulic press, and is subsequently laminated to backing and release film.

EXAMPLE 6

In an IKA recording extruder 46.55 g (24.5% w/w) of Vistanex LM MH, 26.60 g (14.0% w/w) of Vistanex MM L80 and 22.80 g (12.0% w/w) of Eastoflex PLS E1003D are kneaded at 70° C. for 15 minutes. 62.70 g (33.0% w/w) of pulverulent cellulose are added and the mixture is kneaded for 60 minutes. Thereafter 19.00 g (10.0% w/w) of Eutanol G and 11.40 g (6.0% w/w) of DMSO/PVP mixture are added. The mixture is kneaded for 5 minutes, after which 0.95 g (0.5% w/w) of piroxicam are added. The resulting mixture is kneaded at 80–100° C. for a further 60 minutes. The finished composition is then pressed out between release paper, using a hydraulic press, and is subsequently laminated to backing and release film.

EXAMPLE 7

Extrusion

The composition is prepared in a 50 mm Leistritz twin-screw extruder with a throughput of 40 kg/h. The temperature profile for the operation is 130–100° C. from the feed zone to the discharge zone. The ingredients of the adhesive matrix are metered in successively along the entire length of the barrel, in the following order:

| | | | |
|---|---|---|---|
| 1. | Vistanex MM L80: | 4.4 kg/h | solid, granulated |
| 2. | Vistanex LM MH: | 10.4 kg/h | Melt |
| 3. | Eastoflex PLS E1003D: | 5.6 kg/h | Melt |
| 4. | Pulverulent cellulose: | 12.8 kg/h | Solid |
| 5. | DMSO/PVP mixture | 0.8 kg/h | Liquid |
| 6. | Cetiol V | 4.0 kg/h | Liquid |
| 7. | Ibuprofen | 2.0 kg/h | solid |

The composition is prepared continuously and discharged from a slot die. Installed between discharge zone and slot die is a gear pump, which provides for uniform discharge. The adhesive is subsequently coated via a calendar between backing material and a release film and for further processing is wound up into rolls.

The stated substances are as follows:

| Name | Ingredient |
|---|---|
| Kollidon 30 ® | Polyvinylpyrrolidone MW: 44,000 to 54,000 |
| Kollidon 90 ® | Polyvinylpyrrolidone MW: 1,000,000 to 1,5000,000 |
| Vistanex LM MH | Low molecular weight PIB MW: 12,000 to 53,000 |
| Vistanex MM L80 | High molecular weight PIB MW: 750,000 to 1,050,000 |
| Eastoflex PLS E1003D | Amorphous α-polyolefin |
| Cetiol V | Decyl oleate |
| Eutanol G1 | Octyl dodecanol |
| Cellulose Elcema P020 | Pulverulent cellulose |
| Avicel PH 103 | Microcrystalline cellulose |

The matrices in the examples given above all show the advantage that the active substance does not crystallize. Where matrices containing no DMSO/PVP gel are used, complete crystallization of the active substance is found within 1 to 5 days. This leads to a decrease in the release of active substance from the matrix by up to 90%. The incorporation of the gel leads, moreover, to a change in the mechanical properties of the matrix. As the gel fraction goes up the matrices become harder, so that the flow properties of the matrix can be influenced within certain limits. There is likewise an improvement in the permeation of active substance through the skin when the DMSO/PVP gel is employed.

The invention claimed is:

1. A method of preparing a hybridized polymer matrix comprising a polar pharmaceutically active substance, wherein the method comprises
   (a) providing a polymer matrix base which comprises one or more hydrophobic polymers;
   (b) combining the polymer matrix base of (a) with a hybrid system comprising
      (i) dimethyl sulfoxide and
      (ii) one or more substances selected from poly(1-vinyl-2-pyrrolidones) of formula

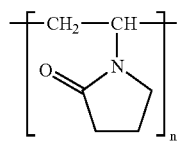

wherein n ranges from 350 to 13,500 and copolymers thereof to provide a matrix base/hybrid system mixture; and
   (c) combining the matrix base/hybrid system mixture of (b) with one or more polar pharmaceutically active substances;
wherein the hybridized polymer matrix is prepared without the use of additional solvents.

2. The method of claim 1, wherein the method is a continuous or batchwise method.

3. The method of claim 1, wherein from 0.1% to 25% by weight, based on a total weight of the hybridized polymer matrix, of the hybrid system are added in (b).

4. The method of claim 1, wherein the hybrid system comprises a gel.

5. The method of claim 1, wherein a weight ratio of (i) to (ii) is from 20:80 to 80:20.

6. The method of claim 5, wherein the weight ratio is 50:50.

7. The method of claim 1, wherein the one or more poly(1-vinyl-2-pyrrolidones) or copolymers thereof have an average molecular weight of from 44,000 to 54,000 g/mol.

8. The method of claim 1, wherein the polymer matrix base comprises a hot melt adhesive.

9. The method of claim 8, wherein the polymer matrix base comprises polyisobutylene.

10. The method of claim 8, wherein the hot melt adhesive comprises a foamed hot melt adhesive.

11. The method of claim 1, wherein the hybridized polymer matrix further comprises one or more fillers.

12. The method of claim 11, wherein the one or more fillers comprise cellulose.

13. The method of claim 1, wherein the one or more pharmaceutically active substances comprise one or more of ibuprofen, nafitine, amorrolfine, tolnaftate, ciclopirox, thymol, eugenol, triclosan, hexachlorophene, benzalkonium chloride, clioquinol, quinolinol, undecenoic acid, ethacridine, chlorhexidine, hexetidine, dodicine, iodine, glycol salicylate, flufenamic acid, etofenamate, ketoprofen, piroxicam, indomethacin, polidocanol, isoprenaline, crotamiton, benzocaine, ammonium bitumasulfonate, urea, and salicylic acid.

14. The method of claim 1, wherein the one or more pharmaceutically active substances comprise a hyperemic substance.

15. The method of claim 1, wherein the one or more pharmaceutically active substances comprise ibuprofen.

16. The method of claim 15, wherein the ibuprofen is added in an amount of from 0.01% to 50% by weight, based on a total weight of the hybridized polymer matrix.

17. The method of claim 15, wherein the ibuprofen is added in an amount of from 0.1% to 20% by weight, based on a total weight of the hybridized polymer matrix.

18. The method of claim 1, wherein from 2% to 9% by weight, based on a total weight of the hybridized polymer matrix, of the hybrid system are added in (b).

19. A method of claim 1, wherein the method further comprises providing a transdermal therapeutic system which comprises the hybridized polymer matrix.

20. The method of claim 19, wherein the transdermal therapeutic system comprises a patch or a bandage.

21. The method of claim 20, wherein the transdermal therapeutic system further comprises a backing.

22. A method of preparing a hybridized polymer matrix comprising a polar pharmaceutically active substance, wherein the method comprises
   (a) providing a polymer matrix base which comprises one or more hydrophobic polymers;
   (b) combining the polymer matrix base of (a) with a hybrid system comprising (i) dimethyl sulfoxide and
(ii) one or more substances selected from poly(1-vinyl-2-pyrrolidones) of formula

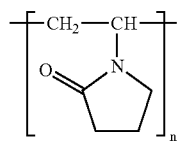

wherein n is such that an average molecular weight of the one or more substances is from 2,000 to 1,500,000 g/mol
to provide a matrix base/hybrid system mixture; and
(c) combining the matrix base/hybrid system mixture of (b) with one or more polar pharmaceutically active substances;
wherein the hybridized polymer matrix is prepared without the use of additional solvents.

* * * * *